(12) United States Patent
Mueller et al.

(10) Patent No.: US 12,109,278 B2
(45) Date of Patent: Oct. 8, 2024

(54) BROAD SPECTRUM SUNBLOCK TRANSFER FILM AND DEVICE

(71) Applicants: Jenni Mueller, Reading, PA (US); Noelle Wolf, Reading, PA (US)

(72) Inventors: Jenni Mueller, Reading, PA (US); Noelle Wolf, Reading, PA (US)

( * ) Notice: Subject to any disclaimer, the term of this patent is extended or adjusted under 35 U.S.C. 154(b) by 0 days.

(21) Appl. No.: 17/657,769

(22) Filed: Apr. 4, 2022

(65) Prior Publication Data

US 2022/0313565 A1 Oct. 6, 2022

Related U.S. Application Data

(60) Provisional application No. 63/200,912, filed on Apr. 2, 2021.

(51) Int. Cl.
*A61K 8/02* (2006.01)
*A61Q 17/04* (2006.01)

(52) U.S. Cl.
CPC ............ *A61K 8/0208* (2013.01); *A61Q 17/04* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 5,352,457 A * | 10/1994 | Jenkins | A61K 9/7061 424/448 |
| 5,682,607 A | 11/1997 | Klein | |
| 6,143,387 A | 11/2000 | Kubler et al. | |
| 8,778,369 B2 | 7/2014 | Ahmed et al. | |
| 8,906,987 B2 | 12/2014 | Denecker | |
| 9,149,668 B2 | 10/2015 | Livacich et al. | |
| 10,463,604 B2 | 11/2019 | Alard et al. | |
| 10,548,821 B2 | 2/2020 | Foley | |
| 10,668,259 B2 | 6/2020 | Jarrell | |
| 10,682,292 B2 | 6/2020 | Newman et al. | |
| 2005/0273901 A1 | 12/2005 | Scheurn et al. | |
| 2006/0030801 A1 * | 2/2006 | Muta | A61L 15/58 602/1 |
| 2007/0231356 A1 | 10/2007 | Berry et al. | |
| 2007/0269496 A1 * | 11/2007 | Gamble | A61P 17/16 424/59 |
| 2018/0030321 A1 | 2/2018 | Tunius | |
| 2019/0368123 A1 | 12/2019 | Quinn et al. | |
| 2021/0000199 A1 | 1/2021 | Kahn | |
| 2021/0137799 A1 | 5/2021 | Watanabe et al. | |

* cited by examiner

*Primary Examiner* — Nannette Holloman
(74) *Attorney, Agent, or Firm* — Dunlap Bennett & Ludwig, PLLC; Anna L. Kinney

(57) ABSTRACT

A broad spectrum sun protection transfer device includes a backing paper; a release coating affixed to the backing paper; and a sun protection transfer film deposited on the release coating. The transfer film is adhesive to skin and opaque to ultraviolet radiation. The transfer film significantly reduces UV radiation penetrating high risk areas of the skin for a long duration of protection.

11 Claims, 3 Drawing Sheets

BROAD SPECTRUM SUNBLOCK TRANSFER FILM AND DEVICE

CROSS-REFERENCE TO RELATED APPLICATION

This application claims the benefit of priority of U.S. provisional application No. 63/200,912, filed Apr. 2, 2021, the contents of which are herein incorporated by reference.

BACKGROUND OF THE INVENTION

The present invention relates to broad spectrum sunscreen and, more particularly, to a broad-spectrum sun protection transfer film and device for high risk areas.

Skin cancer is the most common type of cancer in the world. Current sunscreens do not fully block ultraviolet A (UVA) and ultraviolet B (UVB) rays. For example, Consumer Reports® independently evaluated the sun protection factor (SPF) value of 65 sunscreens and found that 43% of them had less than half the SPF that the label promised. Also, consumer error in application and reapplication, plus external factors such as sand, sweat, and water, prevent lotions from working optimally. Currently available sunscreens only last approximately 90 minutes. As a result, approximately 9,500 people are diagnosed with skin cancer and about 20 people die every day. A comparison of a ten-year span between the 1980s and this past decade showed a 145% and 263% increase in Basal Cell Carcinoma (BCC) and Squamous Cell Carcinoma (SCC), respectively. Specifically, High Risk Areas (HRAs) are the most common areas for BCC and SCC diagnosis. HRAs include the malar region, the dorsal surface of hands, the clavicular chest, the posterior neck, and the upper helices of the ears. HRAs particularly include the ears, nose, and scalp, where 70% of BCC is found, and the face, where SCC is most diagnosed.

As can be seen, there is a need for an easy to apply sunscreen product that fully blocks both UVA and UVB rays in High Risk Areas and is substantially unaffected by external factors such as sweat and water.

SUMMARY OF THE INVENTION

In one aspect of the present invention, a broad spectrum sun protection transfer device, comprises a backing paper; a release coating affixed to the backing paper; and a sun protection transfer film deposited on the release coating, wherein the sun protection transfer film is characterized by adhesiveness to skin and substantial opacity to ultraviolet radiation.

These and other features, aspects and advantages of the present invention will become better understood with reference to the following drawings, description, and claims.

DETAILED DESCRIPTION OF THE INVENTION

Figure 1:
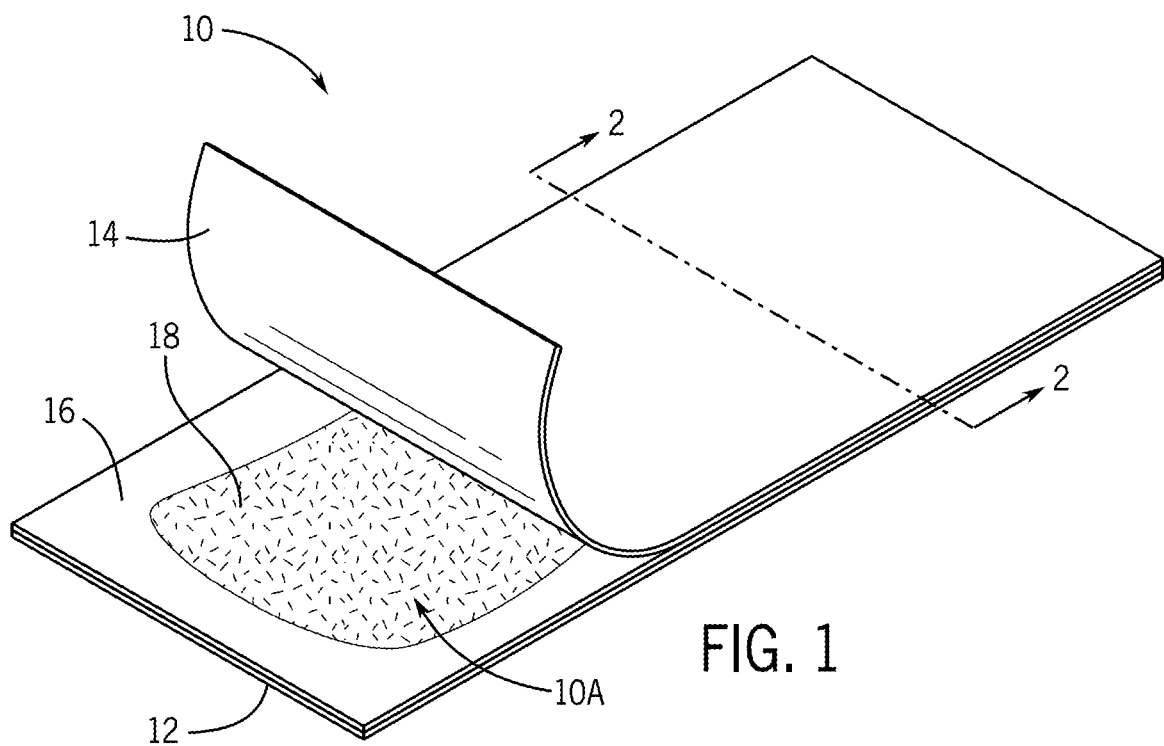
FIG. 1 is a perspective view of an ultraviolet (UV) blocking film according to an embodiment of the present invention.
Figure 2:
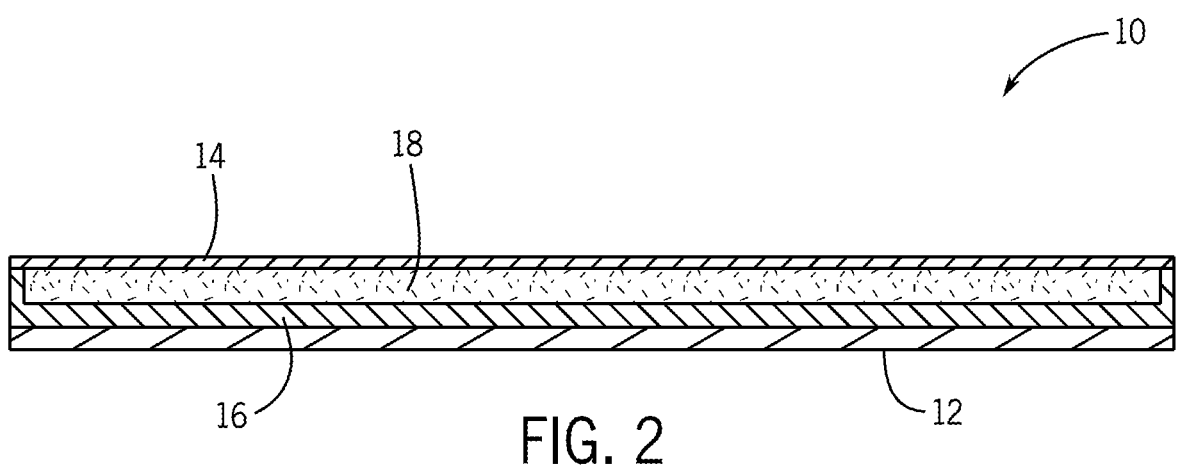
FIG. 2 is a cross-sectional view thereof, taken along line 2-2 of FIG. 1.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

As used herein, the term "backing paper" refers to a release liner or substrate and is not limited to cellulosic fibrous material. Backing paper may also refer to a synthetic polymeric substrate.

The term "release coating" refers to a material, such as but not limited to silicone, coating a backing paper that allows overlay sun protection (OSP), when moistened, to release onto the skin.

"Transfer film" as used herein refers to a film coated onto a release coating. The inventive transfer film is operative to physical block and/or reflect UV radiation and is also referred to as "OSP". OSP may, in some cases, contain a physical UV radiation blocking and/or reflecting agent in a carrier vehicle that adheres to skin. For example, the film may be impregnated with a physical sunblock. The carrier vehicle may include, but is not limited to, for example, the group consisting of: gelatin, polyvinyl alcohol, and/or polyvinyl pyrrolidone, and a combination thereof. Alternatively, the film may have a skin safe, UV blocking and/or reflecting agent printed, coated, or otherwise deposited thereon. Any bonds formed between the transfer film and the release film are overcome by application of water.

As used herein, the term "substantial opacity" indicates that a material prevents or hinders transmission, in this case to UVA and UVB radiation.

Broadly, one embodiment of the present invention is a broad spectrum sun protection transfer device including a transfer film composition comprising one or more sun reflecting ingredients and/or physical sun blocking ingredients (including but not limited to zinc oxide) in a vehicle that adheres to the skin. By utilizing the transfer film in this manner and adhering it to the cutaneous surface of the HRA, the transfer film significantly reduces UV radiation penetrating the skin and provides a significantly longer duration of protection than prior art sunblocks. These ingredients fully protect skin in high-risk areas from UV radiation.

The present invention provides a transfer film or the like, with or without a UV blocking material, that may be safely adhered to the skin in high-risk areas and that retains its composition for longer periods of time than any existing lotion, stick, or spray. This novel application process allows a person's high risk areas to be more fully protected both in duration and in the percentage of UVA and UVB radiation blockage. The transfer film is an element of a sunblock application device sometimes referred to herein as overlay sun protection "OverlaySP (OSP)". OSP is believed to reduce skin cancer diagnosis and photo aging in high-risk areas of the human body by fully blocking UV radiation for a prolonged period without breaking down from sweat or water where it has been applied to the skin. Unlike currently available lotion, cream, stick, and spray sunscreens, the inventive UV protective layer has an indefinite shelf life due to the nature of the ingredients, manufacturing technique, and packaging. The OSP application process is believed to eliminate user error seen with current sunscreen lotion or spray application.

The present invention utilizes transfer film and its components (paper, etc.) in a way that has not been done before. By applying a transfer film over the skin, a novel method of sun protection is achieved, similar to but distinct from UPF achieved with sun protection clothing. This is separate and distinct from all forms of a lotion, cream, stick or spray. The device is novel, in part, because it is a UV protective layer that has an indefinite shelf life due to the nature of the ingredients, manufacturing technique, and packaging.

In some embodiments, OSP may be used decoratively as an artistic statement or for marketing brand collaboration. Other possible biomedical applications, such as measuring vital signs.

The inventive sun protection transfer device is surprisingly superior to currently available types of sun protection, including sun protection compositions in the form of lotions, creams, sticks, and sprays, as well as ultraviolet protection factor (UPF) achieved with sun protection clothing. In fact, the inventive product is applied directly to the top of the skin, bridging the gap between currently available sunscreen and sun protective clothing. An advantage of the inventive device is that the sun protection may be applied just once a day with no need for reapplication. When applied to the skin, OSP maintains its integrity over many hours without breakdown.

The sunblock transfer device comprises a backing paper, a release coating affixed thereon, and a transfer film "OSP" comprising a sun protective vehicle, including adhesives, an UV radiation blocking and/or reflecting ingredient, such as but not limited to the group consisting of: zinc oxide; hypoallergenic, skin-safe inks; hypoallergenic, skin-safe pigments; and combinations thereof. Drying agents and extenders may also be added to modify ink drying behavior. The sunblock transfer device may also have a protective sheet releasably attached to the transfer film.

In some embodiments, the transfer film comprises hypoallergenic, skin-safe pigments. The pigments may enhance consumer experience with the product, for example by more closely approximating the consumer's skin tone.

In some embodiments, the inventive sunblock transfer device is provided as a kit with hypoallergenic removal wipes.

In some embodiments, the sun protection film may be transparent to radiation within the visible light spectrum, yet reflective of ultraviolet radiation. The transparent film may also include skin safe inks.

In some embodiments, a skin safe ink made of physical sun blocking ingredients, such as zinc oxide, and desired color pigment may be printed onto a hypoallergenic transfer film coated onto a backing paper.

The inventive transfer film provides a novel sunblock application process that more fully protects a person's high-risk areas both in duration and in the percentage of UVA and UVB radiation blockage. A method of applying the transfer film may include cleansing the area of skin to which the transfer film will be applied, removing the protective layer, placing the sunblock transfer device against the skin, with the transfer film side down, pressing firmly on the backing paper with a moistened sponge or cloth, and carefully peeling away the backing paper. The user may let the transfer layer dry for about 20 seconds. The transfer film may be removed from the skin by soaking the film in water and mild hypoallergenic face cleanser and gently exfoliating the skin area with a cloth. A removal wipe may be provided to remove any remaining film.

Figure 3:
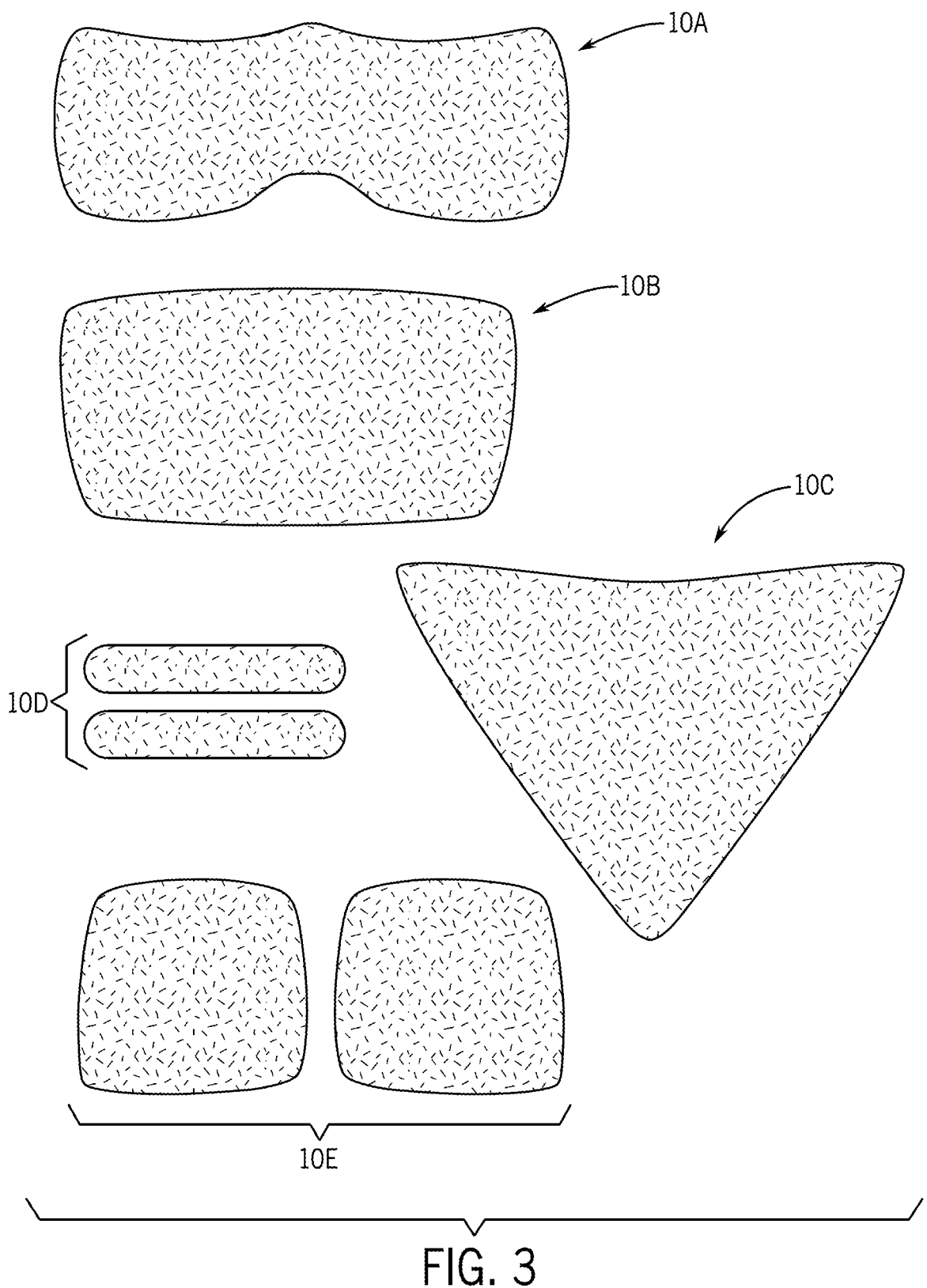
FIG. 3 is a schematic of high-risk area configurations for use of the inventive film.

Referring to FIGS. 1 through 4, FIGS. 1 and 2 illustrate a UV blocking film 10 according to an embodiment of the present invention, for transfer to skin. The film 10 comprises a protective layer 14, a transfer film 18 operative to provide UV protection when applied to skin, a silicone release coating 16, and a backing layer 12. The transfer film 18 of FIG. 1 has a shape configured to protect a high-risk malar area 10A, illustrated in FIG. 3. FIG. 3 also illustrates configurations to protect a high-risk posterior neck area 10B, a high-risk clavicular area 10C, a high-risk helices of the ears area 10D, and a high-risk dorsal surfaces of the hands area 10E. The broad spectrum sun protection transfer device may be a multilayered sheet having regions configured to have shapes corresponding to a template having any of the above-mentioned high-risk areas, including combinations thereof.

Figure 4:
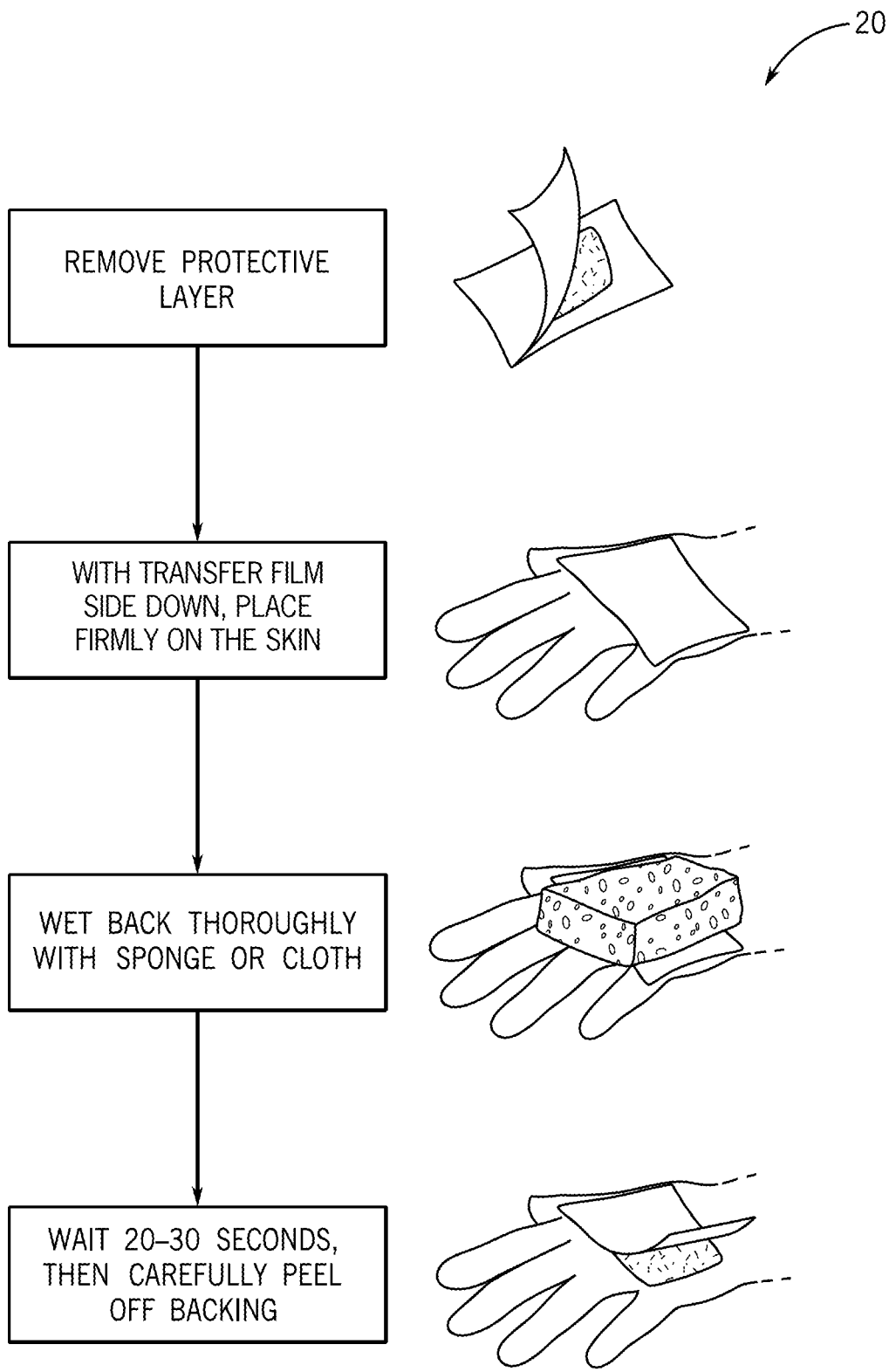
FIG. 4 is a flowchart of a process of using the UV blocking film according to an embodiment of the present invention.

FIG. 4 illustrates a process of applying 20 the UV blocking film 10 of FIG. 1. The protective layer 14 is removed, exposing the transfer film 18. The transfer film 18 is placed on the user's skin. Water is applied to the backing layer 12, which is subsequently peeled away with the silicone release coating 16.

It should be understood, of course, that the foregoing relates to exemplary embodiments of the invention and that modifications may be made without departing from the spirit and scope of the invention as set forth in the following claims.

What is claimed is:

1. A broad spectrum sun protection transfer device, comprising:
   a) a backing paper;
   b) a silicone release coating affixed to the backing paper; and
   c) an overlay sun protection deposited on the silicone release coating, wherein the overlay sun protection is characterized by adhesiveness to skin and substantial opacity to ultraviolet radiation;
   wherein the overlay sun protection is applied by placing the overlay sun protection with transfer film side down, placed against the skin; applying water to the backing paper wetting thoroughly with a sponge or cloth; wait 20-30 seconds; and peeling away the backing paper with the silicone release coating affixed thereto, leaving the overly sun protection adhered to the skin.

2. The broad spectrum sun protection transfer device of claim 1, further comprising a protective sheet releasably attached to the sun protection transfer film.

3. The broad spectrum sun protection transfer device of claim 1, wherein the overlay sun protection is configured to cover a high risk area selected from the group consisting of: malar; posterior neck; clavicular; an ear helix; a dorsal surface of a hand; and a combination thereof.

4. The broad spectrum sun protection transfer device of claim 1, wherein the broad spectrum sun protection transfer device is a layered sheet having regions configured to have shapes corresponding to a template of high risk areas selected from the group consisting of: malar; posterior neck; clavicular; a helix of an ear; a dorsal surface of a hand; and a combination thereof.

5. The broad spectrum sun protection transfer device of claim 1, characterized in that the sun protection transfer film is operative to reflect UV radiation.

6. The broad spectrum sun protection transfer device of claim 5, wherein the overlay sun protection is transparent to radiation in a visible light spectrum.

7. The broad spectrum sun protection transfer device of claim 1, characterized in that the overlay sun protection is operative to physically block UV radiation.

8. The broad spectrum sun protection transfer device of claim 7, wherein the overlay sun protection comprises a UV radiation blocking ingredient selected from the group consisting of zinc oxide; a hypoallergenic, skin-safe pigment; a hypoallergenic, skin-safe ink; and combinations thereof.

9. The broad spectrum sun protection transfer device of claim 1, wherein the overlay sun protection comprises a carrier vehicle.

10. The broad spectrum sun protection transfer device of claim 9, wherein the carrier vehicle is selected from the group consisting of: gelatin; polyvinyl alcohol; polyvinyl pyrrolidone; and combinations thereof.

11. The broad spectrum sun protection transfer device of claim 1, wherein the silicone release coating is a second layer fastened between a first layer comprising the backing paper and a third layer comprising the overlay sun protection, and wherein a surface of the third layer opposite the second layer is configured to be placed on the skin.

\* \* \* \* \*